United States Patent [19]

Mische

[11] Patent Number: 5,376,083
[45] Date of Patent: Dec. 27, 1994

[54] STEERABLE INFUSION GUIDE WIRE

[75] Inventor: Hans A. Mische, St. Cloud, Minn.

[73] Assignee: Lake Region Manufacturing Company, Inc., Chaska, Minn.

[21] Appl. No.: 62,441

[22] Filed: May 14, 1993

Related U.S. Application Data

[63] Continuation of Ser. No. 607,454, Oct. 31, 1990, Pat. No. 5,211,636.

[51] Int. Cl.$^5$ .............................................. A61M 5/00
[52] U.S. Cl. ..................................... 604/264; 128/772
[58] Field of Search ................. 604/264, 53, 164–169, 604/170; 128/657, 656, 778, 772

[56] References Cited

U.S. PATENT DOCUMENTS

| | | | |
|---|---|---|---|
| 3,612,058 | 10/1971 | Ackerman | 128/772 |
| 4,763,647 | 8/1988 | Gambole | 128/657 |
| 4,815,478 | 3/1989 | Buchbinder et al. | 128/772 |
| 4,932,419 | 6/1990 | de Toledo | 128/772 |
| 5,154,705 | 10/1992 | Fleischhacker et al. | 128/772 |
| 5,165,421 | 11/1992 | Fleischhacker et al. | 128/772 |
| 5,211,636 | 5/1993 | Mische | 604/264 |

Primary Examiner—C. Fred Rosenbaum
Assistant Examiner—Manuel Mendez
Attorney, Agent, or Firm—Grady J. Frenchick

[57] ABSTRACT

A guide wire having state-of-the-art handling characteristics for ease in positioning a variety of catheters and other devices within the cardiovascular or other body system wherein the guide wire is also suitable for infusion of small volumes of fluid. The exceedingly small diameter guide wire has unique infusion properties. The guide wire body has at least one helical coil having a flexible nonporous sheath within the lumen. The helical coil is close wound along the majority of its length. The distal end of the helical coil has spaced windings to permit infusion of the fluid. The flexible nonporous sheath terminates proximal to the space wound portion. The solid core wire, which runs the entire length of the guide wire, is located within the same lumen used for infusion. This provides a greatly increased surface area in relation to the cross sectional area of the infusion lumen ensuring a slow but extremely constant infusion rate over a wide range of infusion pressures.

18 Claims, 13 Drawing Sheets

STEERABLE INFUSION GUIDE WIRE

CROSS REFERENCE TO CO-PENDING APPLICATIONS

This application is a continuation of Ser. No. 607,454 filed Oct. 31, 1990 now U.S. Pat. No. 5,211,636.

The present application also is related to U.S. patent application Ser. No. 120,878, entitled Hollow Lumen Cable Apparatus, and filed Sep. 30, 1987, in the name of Fleischhacker, Jr.; and U.S. patent application Ser. No. 07/384,398, entitled Hollow Lumen Cable Apparatus, and filed Jul. 24, 1989, in the name of Fleischhacker, Jr., both assigned to the assignee of the present application.

BACKGROUND OF THE INVENTION

1. Field of the Invention

The present invention relates generally to medical devices, and more particularly, relates to guide wires used for infusion of fluids.

2. Description of the Prior Art

The use of guide wires to easily and properly position diagnostic, therapeutic, and infusion catheters has been known for some time. The above cross referenced commonly assigned patent applications, herein incorporated by reference, describe the state of the art in the design, manufacture, and use of guide wires.

One of the purposes for such guide wires is the positioning of infusion catheters. This procedure requires the attending medical personnel to insert the guide wire into the vascular system through a puncture at a convenient location. The guide wire is normally advanced under fluoroscopy until its distal tip is located at the desired infusion site. The infusion catheter is then advanced over the guide wire until the infusion orifice(s) is located at the infusion site. Oftentimes the guide wire is removed to make the entire cross-sectional area of the infusion catheter lumen available for the passage of fluid.

Because of the difficulties with this procedure, attempts have been made to make an infusion catheter which requires no separate guide wire. U.S. Pat. No. 3,757,768 issued to Kline describes one approach to such a catheter. The Kline design uses a spring guide over which is placed a sheath. To improve the handling characteristics, a removable stylet is inserted into the central infusion lumen. The stylet must be removable to provide the desired infusion properties. However, because it is removable, it is not available to transfer axial torque.

SUMMARY OF THE INVENTION

The present invention overcomes the problems associated with the prior art by providing a steerable infusion guide wire having all of the advantages of a steerable guide wire wherein the central lumen is used for infusion of a fluid. Because the device is a guide wire, it can also be used for placement of other devices (e.g., catheters, balloons, sensors, etc.) by removing the standard fluid coupling (i.e., Touhy-Borst connector) from the proximal end. The body of the guide wire has at least one outer spring coil with a solid inner core wire running the entire length. This structure is excellent for the transmission of torque from proximal to distal end. A flexible sheath within the outer spring coil ensures that the structure does not leak proximal to the infusion site. Placement of the flexible sheath inside, rather than outside of the outer coil, minimizes interference of the sheath with torque transmission through the coil.

The main body of the spring coil is close wound for maximum control. The spring coil may be space wound at the distal end, however, to provide infusion ports. Infusing fluid through the coils permits the spring coil to run to the distal tip of the device providing the desired distal steerability.

The central lumen containing the permanent core wire is used for passage of the infusion fluid. The core wire is tapered at the distal end to enhance handling characteristics of the guide wire. This also increases the cross-sectional area of the central lumen available to the infusion liquid creating a reverse venturi effect and causing the fluid to weep from the infusion ports at a constant rate for a constant infusion pressure. Because the cross-sectional area is highly influenced by the degree of taper of the core wire, the infusion rate at a given pressure is thereby controllable. The system is particularly efficient for precise dispensing of highly concentrated fluids at remote locations.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
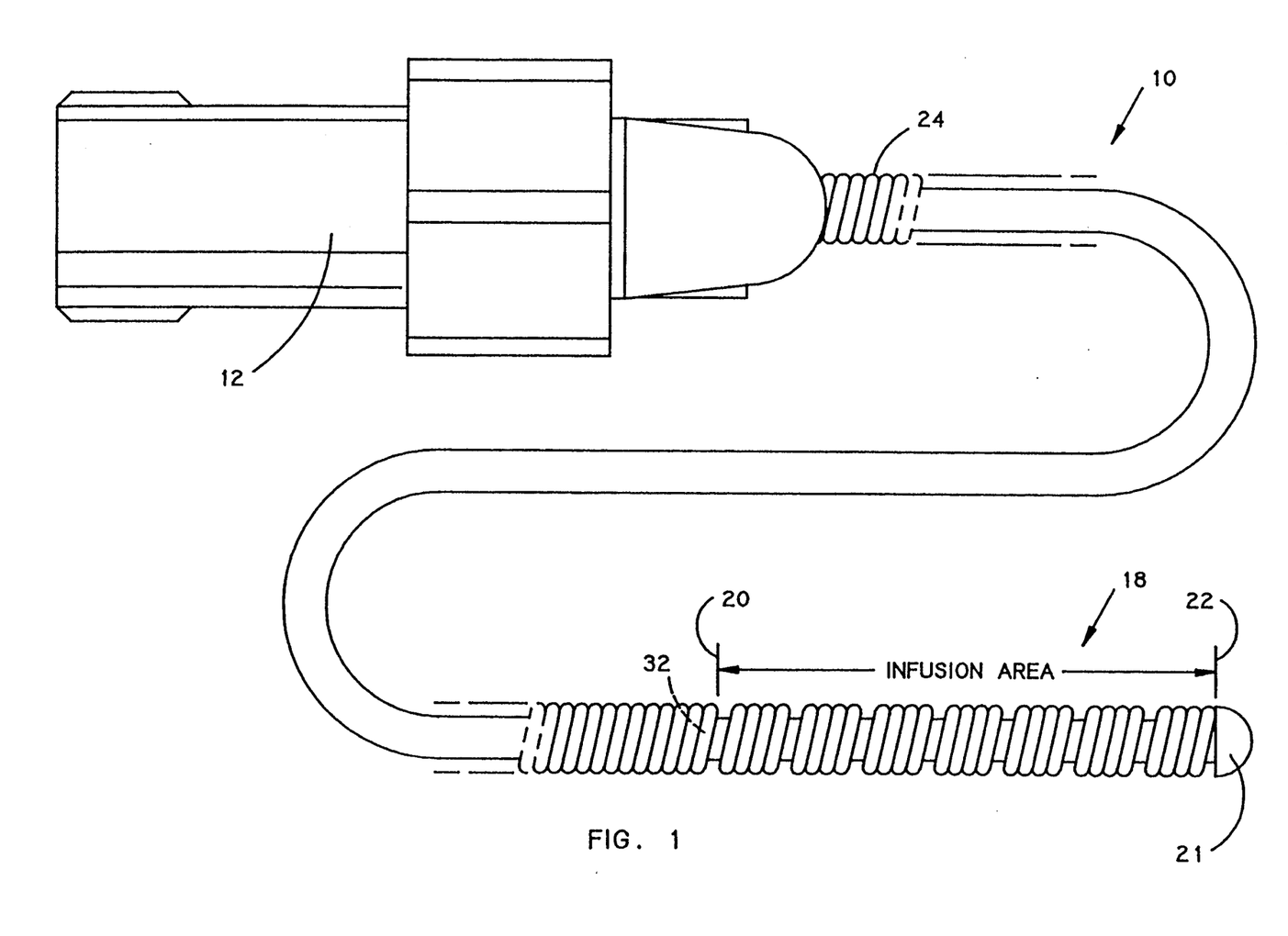
FIG. 1 is a conceptual view of an infusion guide wire according to the present invention.

FIG. 1 is a conceptual view of an infusion guide wire 10 employing the present invention. The outer surface of the main body of infusion guide wire 10 is a close wound coil as shown. A syringe or other pump system may be sealingly coupled to the proximal end of infusion guide wire 10 by standard Touhy-Borst connector 12. A proximal tip is also welded, brazed, or soldered in such a fashion as to allow pressurized fluid to enter the inner lumen. Touhy-Borst connector 12 can be removed to allow the infusion guide wire 10 to function as an ordinary guide wire to facilitate placement of other devices (e.g., catheters). In the preferred mode, and not to be deemed as limiting of the invention, the fluid to be infused (not shown) is loaded into a syringe in the normal fashion and is pressurized with manual force applied to the thumb knob attached to a piston (not shown).

The pressurized fluid is conveyed through the body of infusion guide wire 10 to infusion area 18 located at the distal end. Infusion area 18 is designed for release of the pressurized fluid from point 20 to point 22 as described below. Solid distal tip 21 is formed in the manner known in the art by welding, brazing, soldering, etc.

Figure 2:
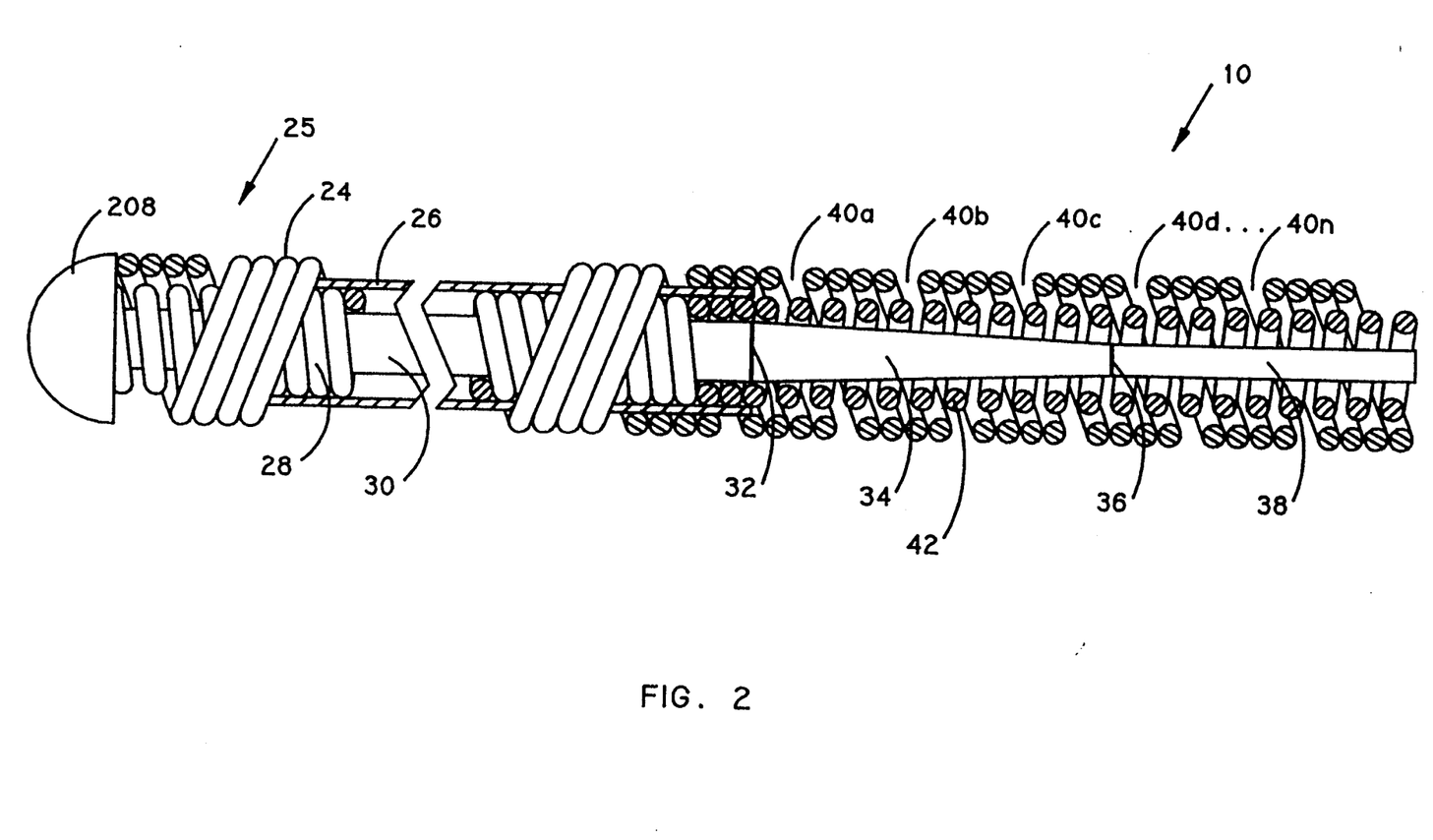
FIG. 2 is a partially sectioned view of the preferred embodiment of the present invention.

FIG. 2 is a partially sectioned view of the preferred embodiment of the present invention. The interior of infusion guide wire 10 contains solid core wire 30 having a constant diameter along substantially its entire length. However, the handling characteristics of infusion guide wire 10 is improved by tapering solid core wire 30 beginning at point 32 which is about 5 cm from the distal tip. The taper initiated at point 32 results in constant intermediate diameter 34. Solid core wire 30 is further tapered beginning about 2 cm from the distal tip at point 36 to final diameter 38. Solid core wire 30 serves to transmit torque efficiently.

Solid core wire 30 runs the entire length of the lumen of inner coil 28. Inner coil 28 is preferably a spring coil of stainless steel wire having a unifilar or multifilar configuration which is close wound to near point 32. The proximal end and that portion distal to point 32 of inner coil 28 are spaced to permit infusion of the pressurized fluid.

Covering inner coil 28 at the distal end of standard Touhy-Borst connector 12 (not shown) to near point 32 is flexible sheath 26 which is preferably a thin non-porous polymer, silicone rubber or PTFE sleeve. Flexible sheath 26 ensures that pressure is maintained from standard Touhy-Borst connector 12 to infusion area 18.

The outer layer of infusion guide wire 10 consists of outer coil 24, which is also a quadrifilar stainless steel coil. It is wound to the opposite pitch of inner coil 28 to improve the torque transmission characteristics of infusion guide wire 10. As with inner coil 28, outer coil 24 is close wound between standard Touhy-Borst connector 12 and the distal end beginning at point 32. Outer coil 24 is similarly space wound distal to point 32 to permit infusion of the fluid. The infusion fluid is dispensed via infusion ports 40a–40n formed by the spaces in outer coil 24. Semi-hemispherical weld 208 fixedly attaches outer coil 24, inner coil 28, and solid core wire 30.

The relatively small free cross-sectional area within the lumen of inner coil 28, which is not occupied by solid core wire 30, is used for passage of the infusion fluid. This free cross-sectional area is increased distal to point 32 as a result of the tapering of solid core wire 30. The increased volume at the distal tip creates a reverse venturi effect causing an extremely constant fusion rate at a given infusion pressure. The degree of taper controls that infusion rate because of the large impact it has upon free cross-sectional area.

Flexible sheath 26 is located between outer coil 24 and inner coil 28 in the preferred embodiment. Having flexible sheath 26 inside of outer coil 24 prevents flexible sheath 26 from interfering with the torque transmission properties of outer coil 24.

Figure 3:
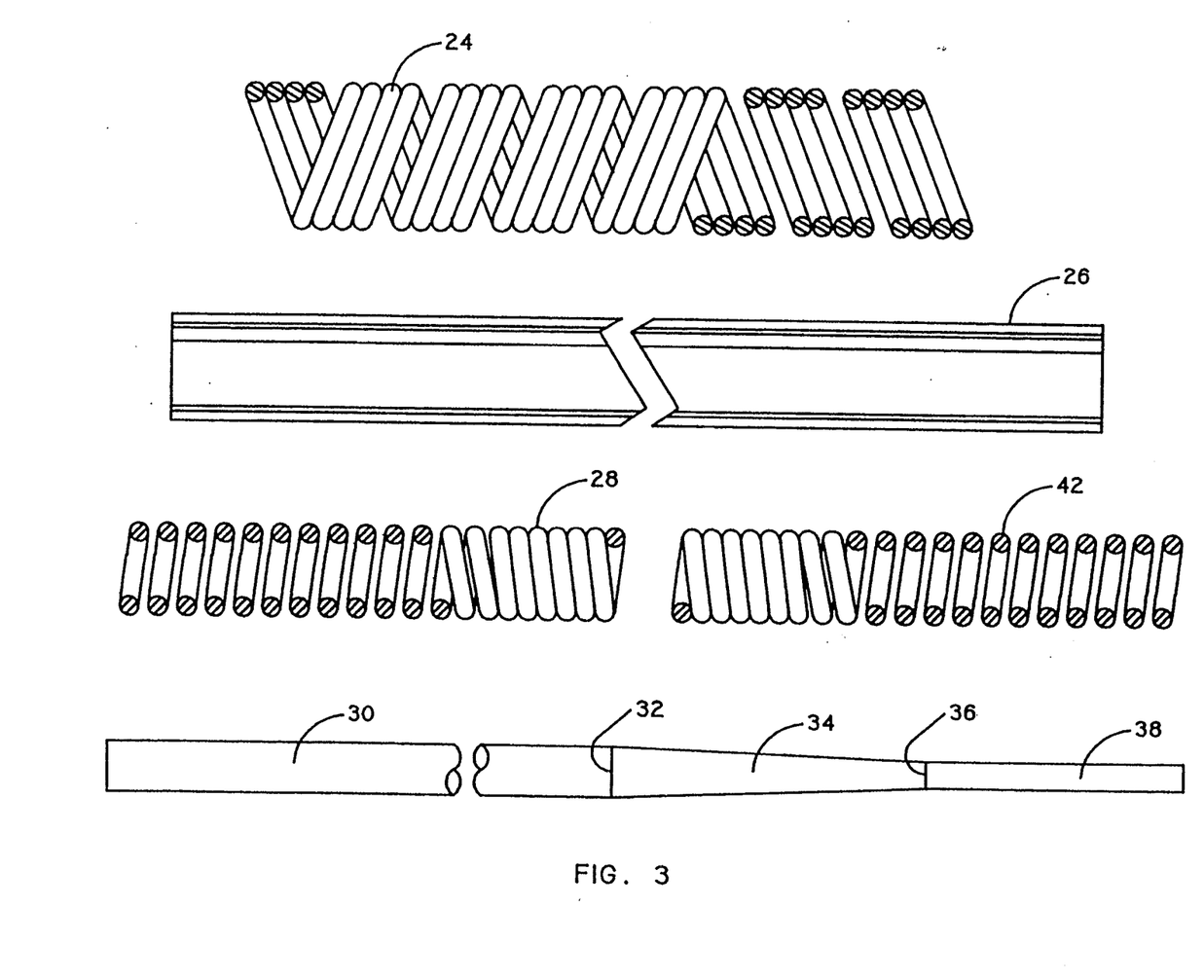
FIG. 3 is an exploded view of the components of the infusion guide wire of FIG. 2.

FIG. 3 is an exploded view of the major components of the preferred embodiment of infusion guide wire 10. All elements are as previously described.

Figure 4:
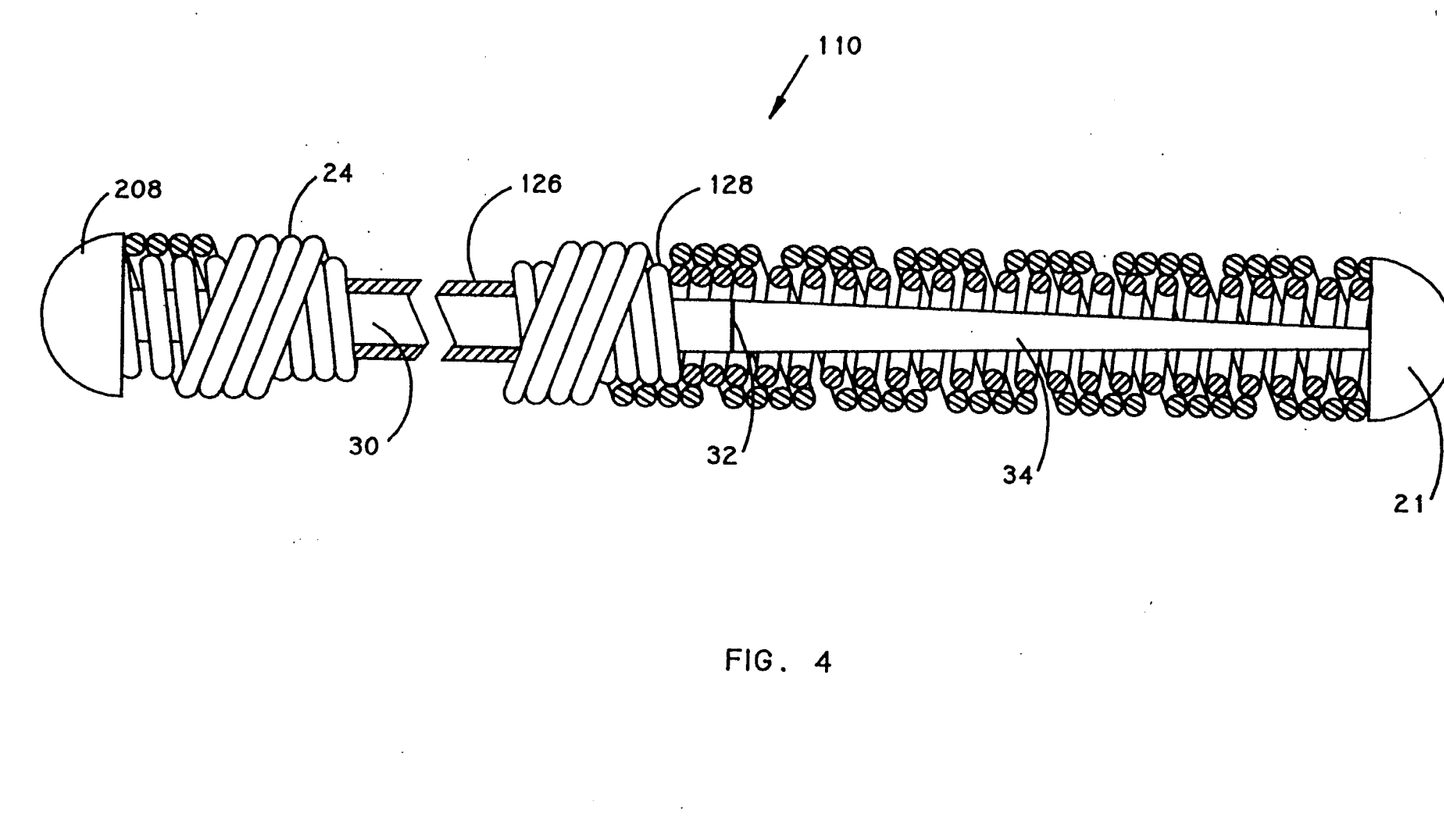
FIG. 4 is a partially sectioned view of an alternative embodiment of the present invention.

FIG. 4 is a partially sectioned view of a first alternative embodiment, infusion guide wire 110, of the present invention. This embodiment is the same as the preferred embodiment except that flexible sheath 26 is deleted and its function is replaced with flexible sheath 126 located within the lumen of inner coil 128. In this embodiment, the infusion fluid contacts the surface of flexible sheath 126 and solid core wire 30 only. This produces less cohesion because the infusion fluid does not contact inner coil 128. Infusion guide wire 110, therefore, requires less infusion pressure for a given infusion volume. However, it appears slightly stiffer as it is advanced through the cardiovascular system as outer coil 24 and reverse wound inner coil 128 are in direct contact. This may be desirable as inner coil 128 and outer coil 24 lock down better for more direct torque transmission. Other components of infusion guide wire 110 are as previously described.

Figure 5:
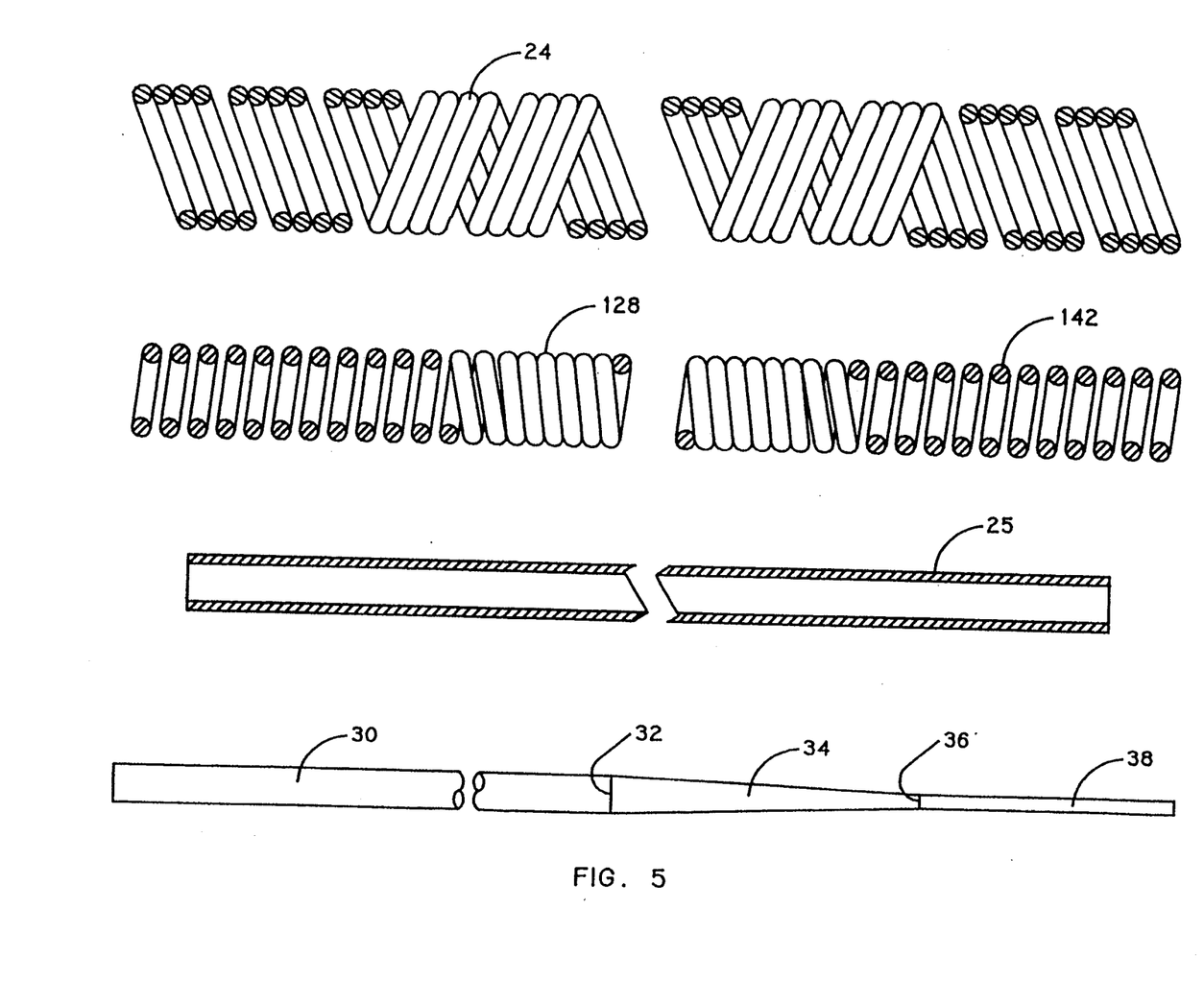
FIG. 5 is an exploded view of the components of the infusion guide wire of FIG. 4.

FIG. 5 is an exploded view of the major components of infusion guide wire 110. All components are referenced above.

Figure 6:
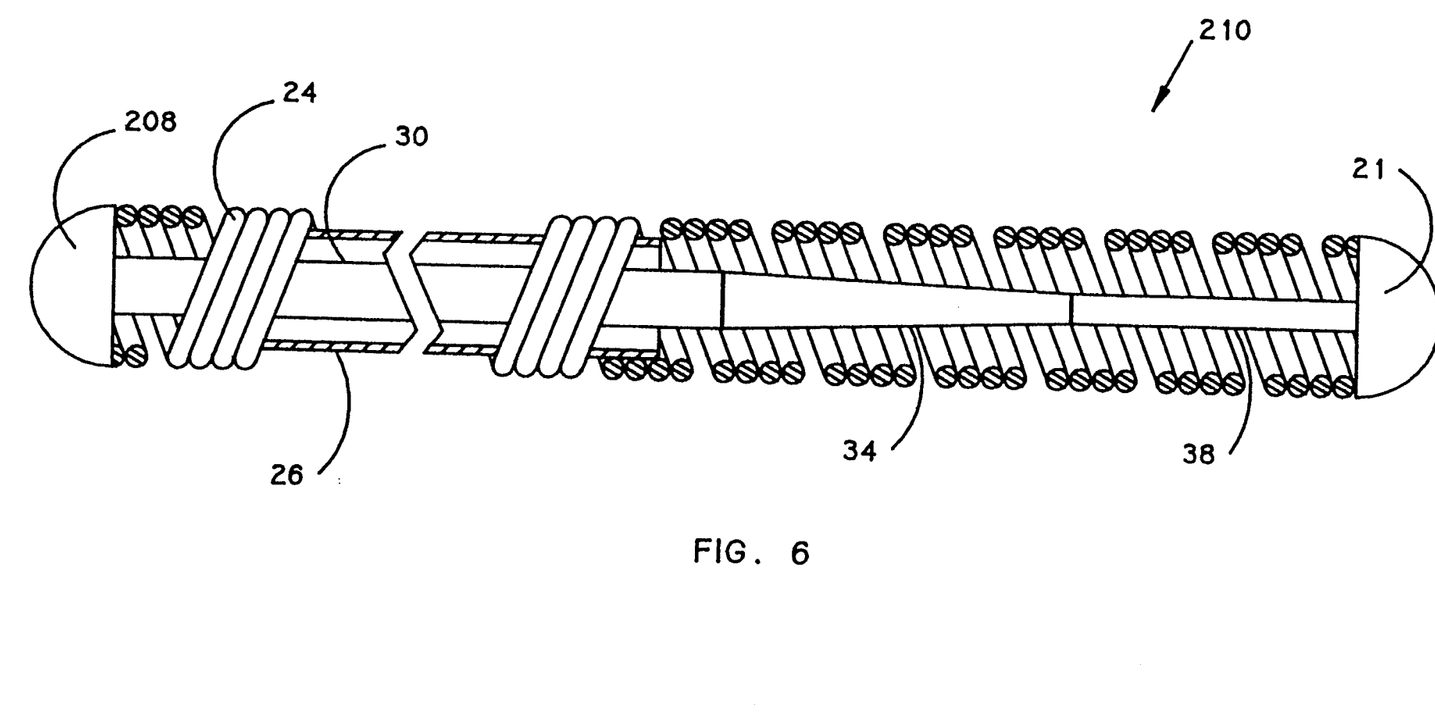
FIG. 6 is a partially sectioned view of a second alternative embodiment of the present invention.

FIG. 6 is a partially sectioned view of a second alternative embodiment, infusion guide wire 210, of the present invention. Infusion guide wire 210 is similar to infusion guide wire 10 except that inner coil 28 (see also FIG. 2) is eliminated. The resulting structure is more easily fabricated and can be made with smaller dimensions for a given infusion rate because it has fewer components. It is more difficult to transmit torque over infusion guide wire 210 because of the absence of the second reverse wound coil. The infusion characteristics of infusion guide wire 210 are similar to infusion guide wire 110 because the infusion fluid contacts only flexible sheath 26 and solid core wire 30.

Figure 7:
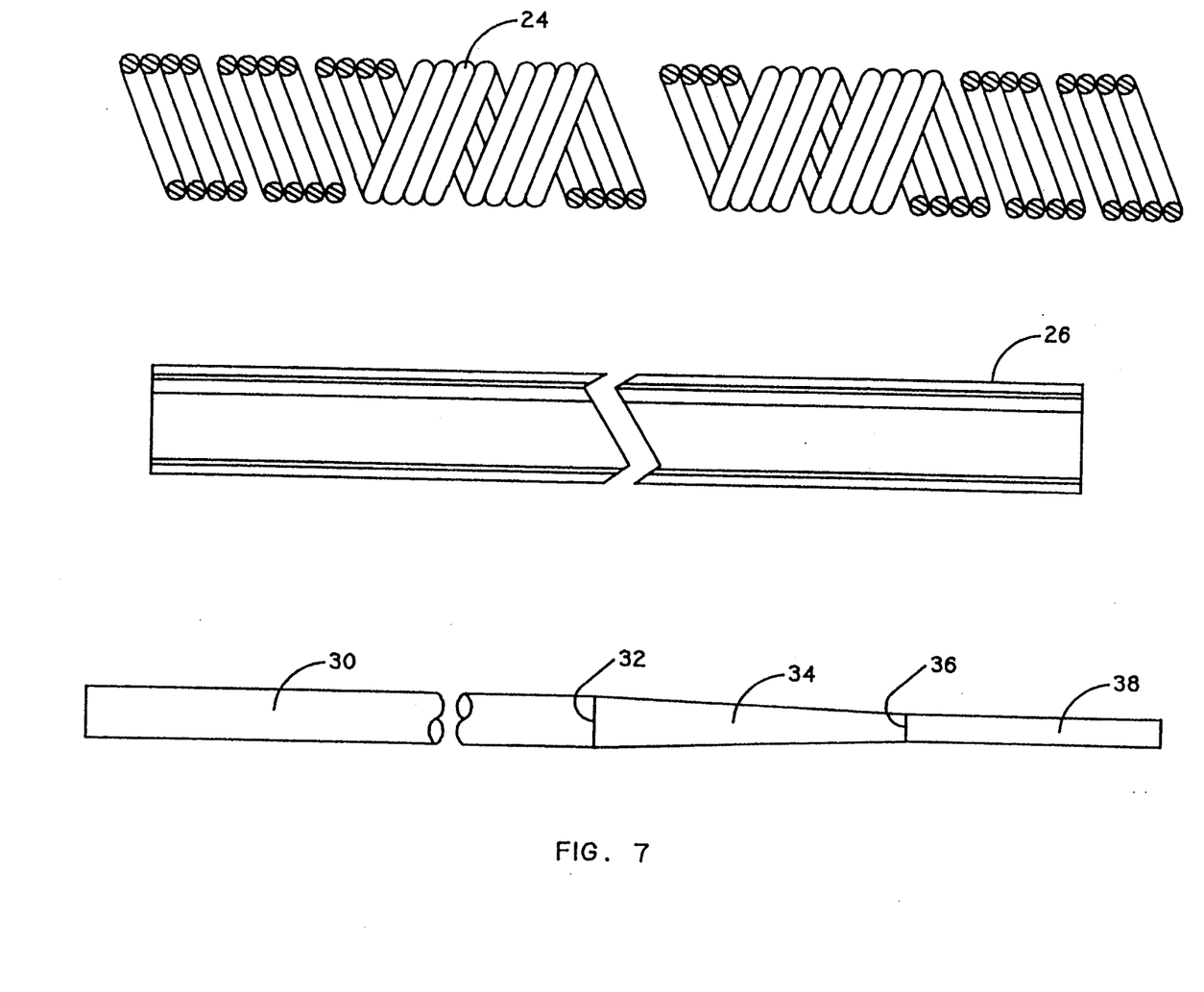
FIG. 7 is an exploded view of the components of the infusion guide wire of FIG. 6.

FIG. 7 is an exploded view of the major components of infusion guide wire 210. All referenced elements are as previously described.

Figure 8:
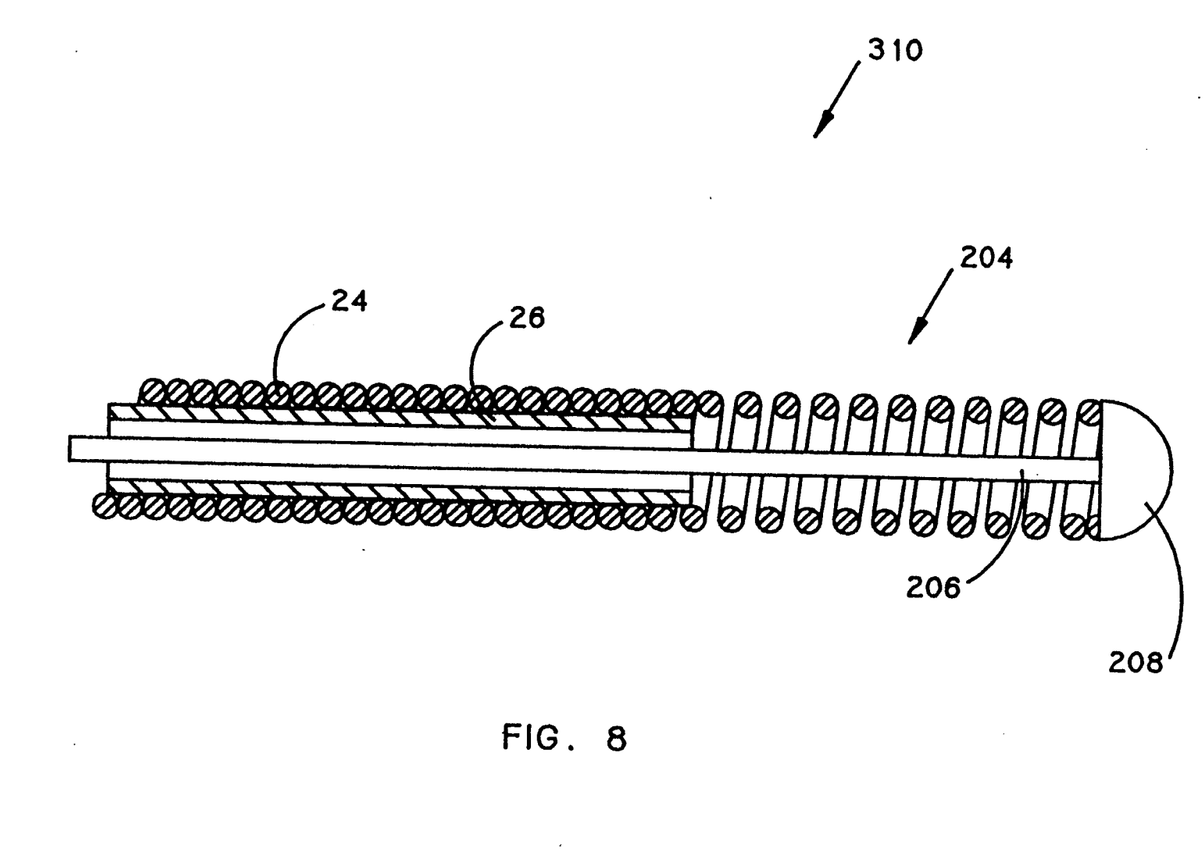
FIG. 8 is a sectioned view of the distal tip of a third alternative embodiment.

FIG. 8 is a sectioned view of infusion guide wire 310, which is a third alternative embodiment of the present invention. Infusion guide wire 310 is similar to infusion guide wire 210 except that it employs a single filar rather than a quadrifilar outer coil 24 providing handling characteristics associated with a single filar guide wire. This embodiment also employs a core wire 206 having a constant diameter over its entire length. Infusion occurs from relatively constant sized infusion ports at area 204. Semi-hemispherical weld 208 is normally a smooth weld or brazing of the distal tip of the metallic components.

Figure 9:
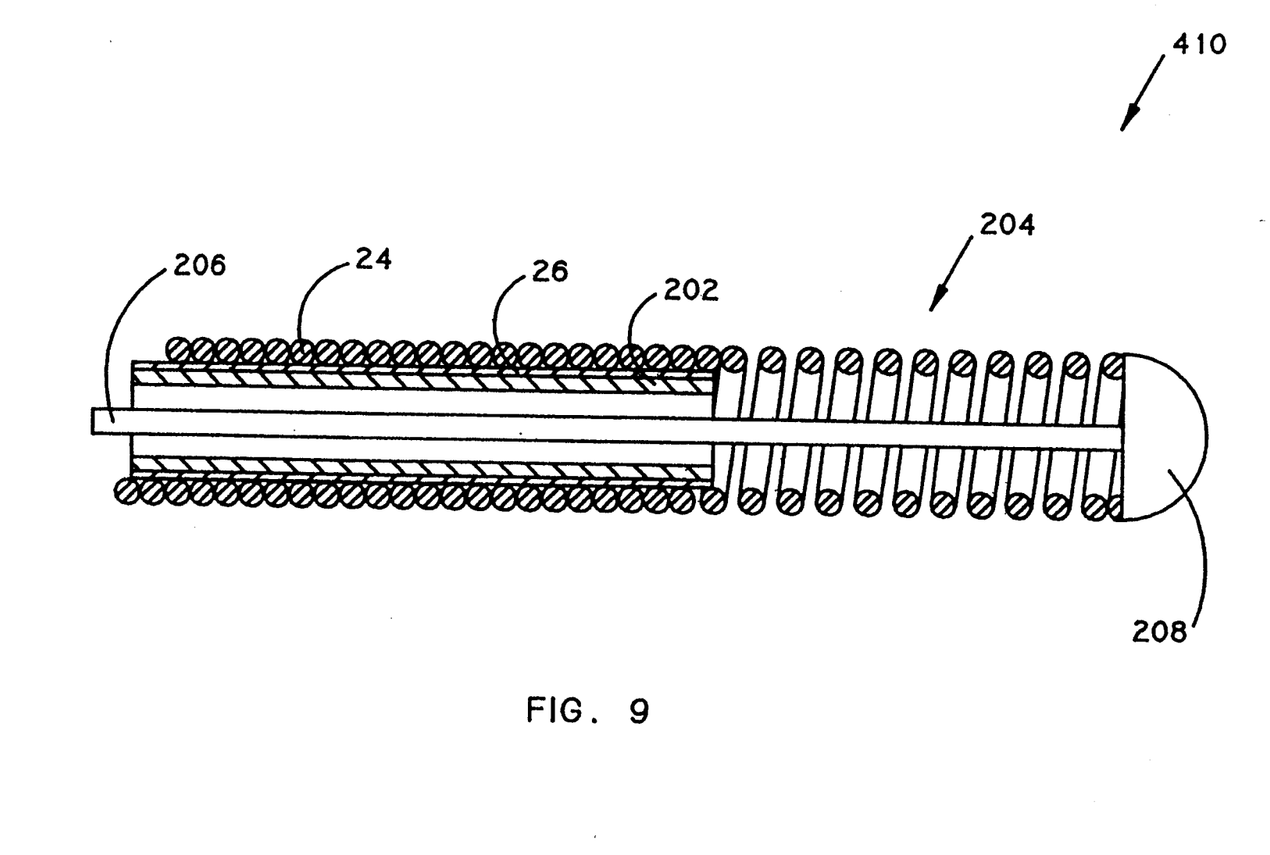
FIG. 9 is a sectional view of the distal tip of a fourth alternative embodiment.

FIG. 9 is a sectioned view of the distal end of infusion guide wire 410 which is a fourth alternative embodiment of the present invention. This embodiment is constructed as infusion guide wire 310 with the addition of inner capillary tube 202. This tubing is available from Poly-Micro Technologies, Inc. as Flexible Fused Silica Capillary Tubing.

Figure 10:
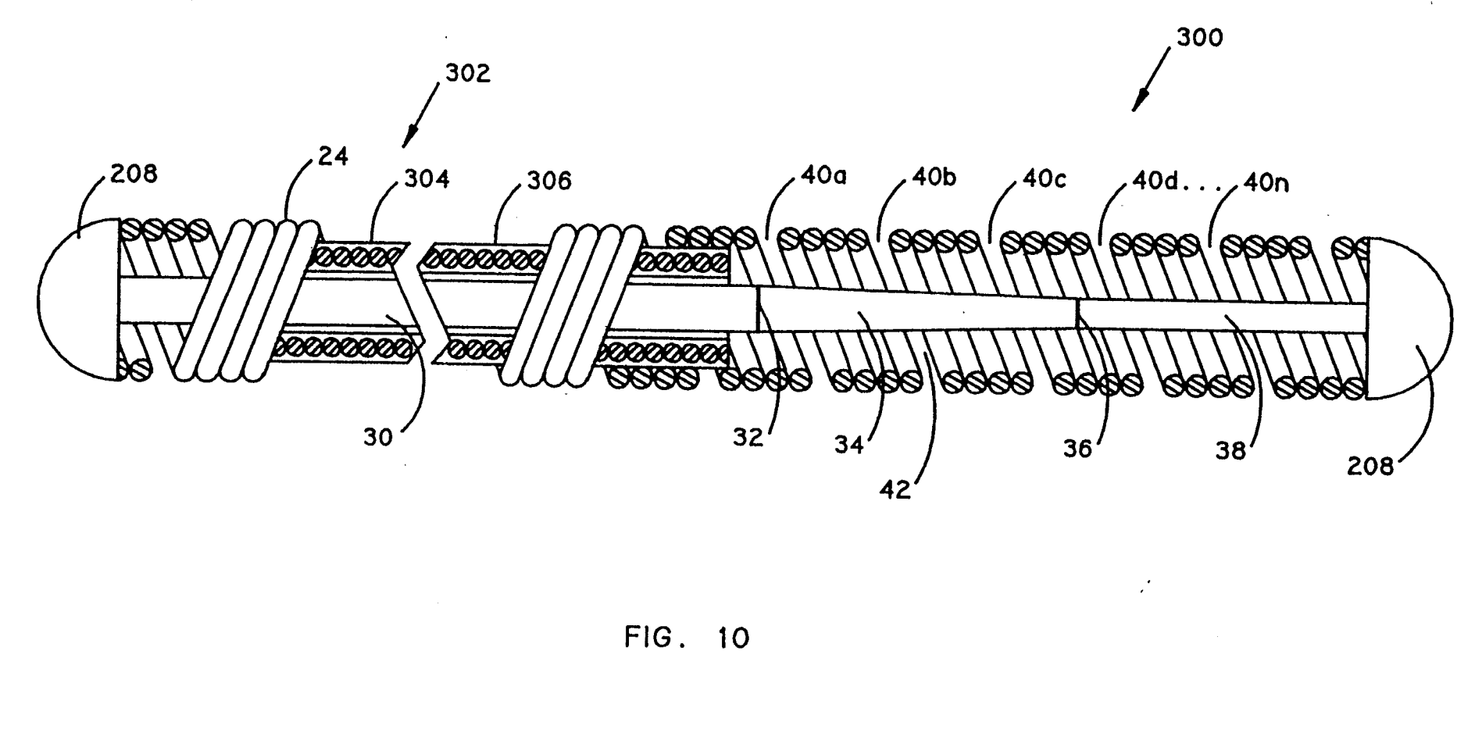
FIG. 10 is a partially sectioned view of a fifth alternative embodiment.

FIG. 10 is a partially sectioned view of a guide wire 300, employing a fifth alternative embodiment of the present invention. This embodiment is similar to the preferred embodiment except that an inner coil 306 is encapsulated within flexible sheath 304 to produce inner assembly 302. The use of inner assembly 302 provides the advantages of using a two coil structure (see also FIG. 2, for example), but provides a larger internal infusion lumen for a given outside diameter, because the functions of two layers (i.e. the flexible sheath and the inner coil) are accomplished with a single layer (i.e. inner assembly 302). All other components are as previously described.

Figure 11:
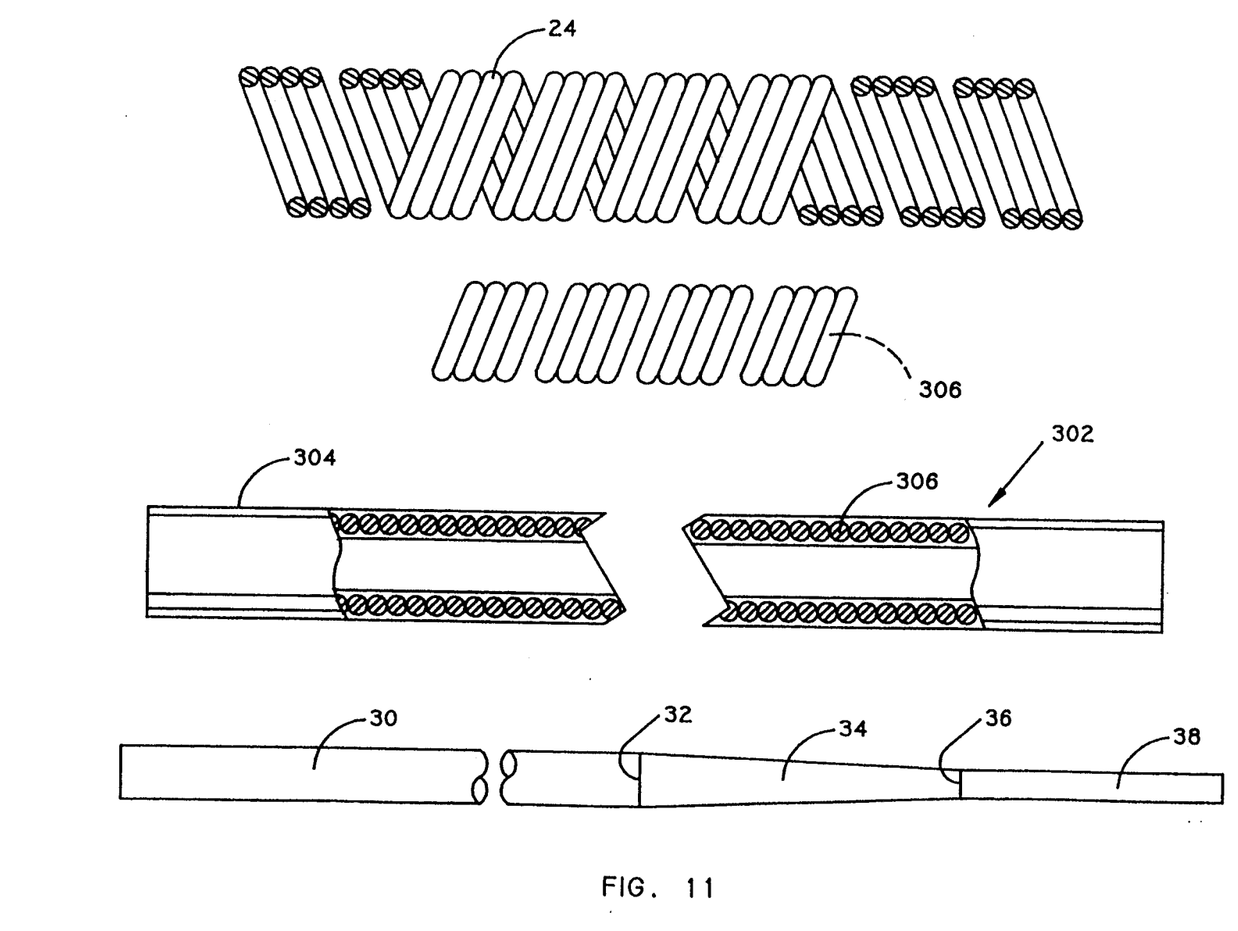
FIG. 11 is an exploded view of the main components of the fifth alternative embodiment.

FIG. 11 is an exploded view of the major components of guide wire 300 of FIG. 10. Even though inner coil 306 is shown as a helical wound coil, it may also be a braided structure of appropriate stiffness and strength. Inner coil 306 (or alternative braided structure) is encapsulated within flexible sheath 304 by molding, dipping, or other suitable attachment means.

Figure 12:
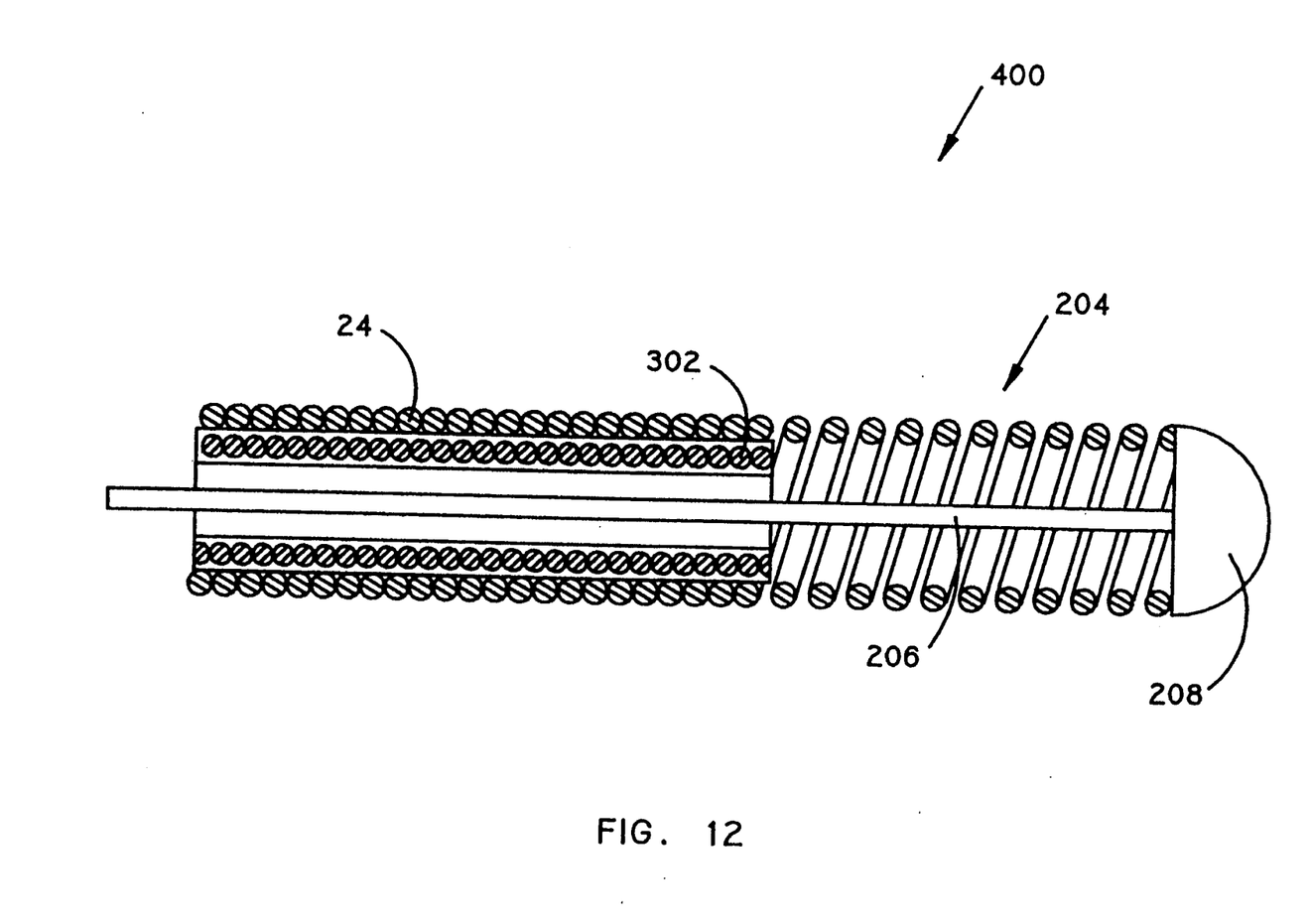
FIG. 12 is a sectioned view of the distal tip of a sixth alternative embodiment; and, FIG. 13 is a sectioned view of the distal tip of a seventh alternative embodiment.

FIG. 12 is a sectioned view of the distal tip of guide wire 400 employing a sixth alternative embodiment of the present invention. This embodiment is similar in construction and operation to the embodiment of guide wire 300 (see also FIG. 10) except outer coil 24 is single filar. This produces the smooth, evenly spaced infusion ports at area 204. Outer coil 24 may, of course, be wound in other configurations without limiting the present invention. The present embodiments are provided by way of example only.

Figure 13:
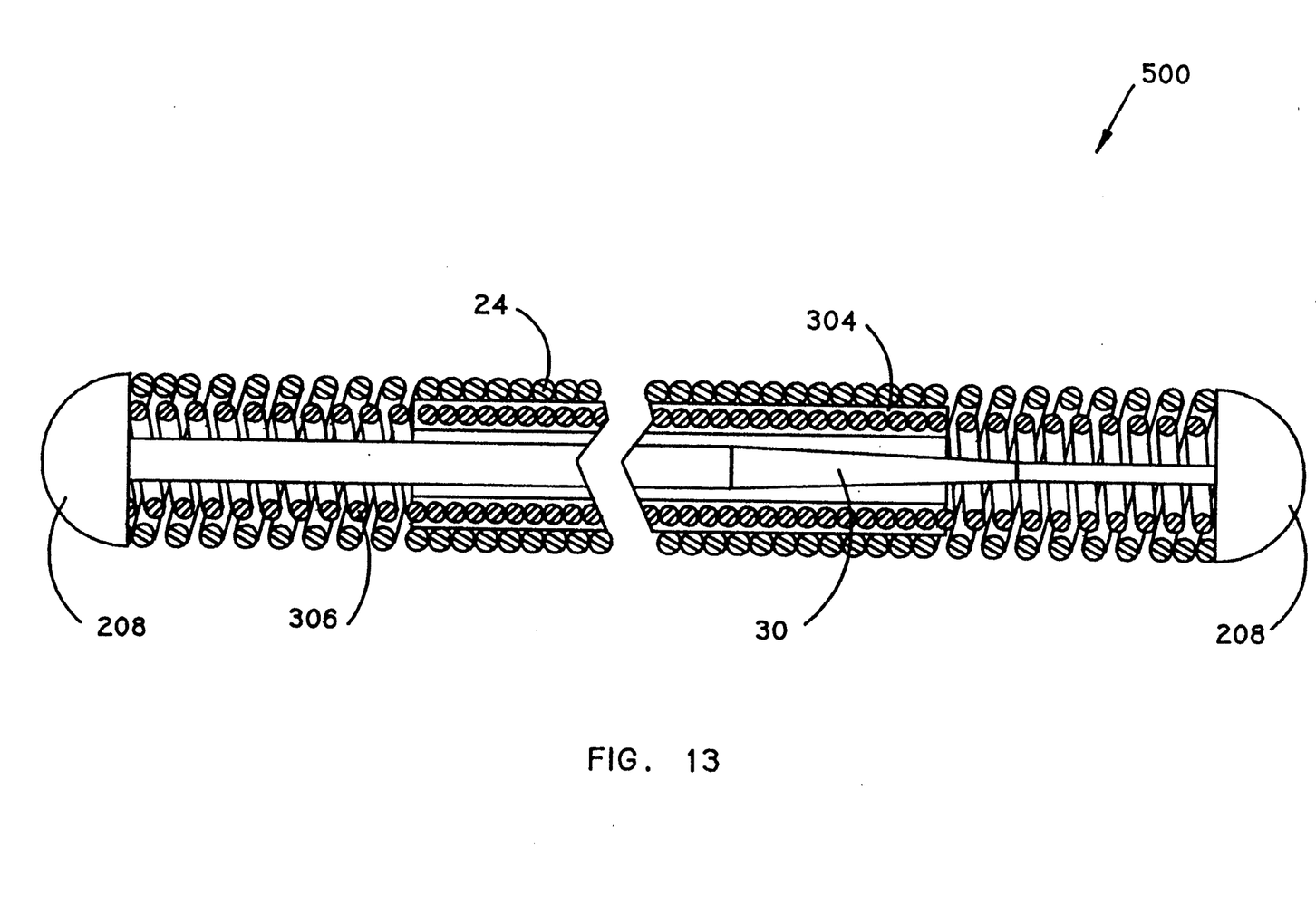

FIG. 13 is a cross-sectional view of the distal tip of guide wire 500 incorporating a seventh embodiment of the present invention. This embodiment is similar to the structure of infusion guide wire 400 (see also FIG. 12) except inner coil 306 extends proximally and distally of flexible sheath 304. The resulting guide wire 500 is similar to the embodiments of FIGS. 2 and 4 except that the cross-sectional size is smaller for a given lumen size.

Having thus described a number of embodiments of the present invention, those of skill in the art will be able to apply the teachings found herein to yet other embodiments within the scope of the claims hereto attached.

I claim:

1. An infusion guide wire having a proximal end and a distal end comprising:
   a. an outer coil having a proximal end and a distal end and having a first lumen;
   b. a flexible sheath having a proximal end and a distal end and having a second lumen located within said first lumen, said flexible sheath not being coterminous with the distal end of the outer coil;
   c. a core wire having a distal and proximal end fixedly attached to said distal and proximal end respectively of said outer coil located within said second lumen;
   d. a distal tip marker; and
   e. means sealingly attached to said proximal end of said flexible sheath for inserting a pressurized fluid into said second lumen wherein said outer coil is space wound from the distal end of said flexible sheath to said distal end of said outer coil.

2. An infusion guide wire according to claim 1 wherein said outer coil is close wound for the majority of its length between said proximal and said distal end.

3. An infusion guide wire according to claim 2 further comprising a capillary tube within said second lumen.

4. An infusion guide wire according to claim 1 wherein said outer coil is quadrifilar.

5. An infusion guide wire according to claim 1 wherein said outer sheath is single filar.

6. An infusion guide wire according to claim 1 further comprising an inner coil having a third lumen located within said first lumen wherein said outer coil and said inner coil are oppositely wound.

7. An infusion guide wire according to claim 6 wherein said inner coil is located within said second lumen.

8. An infusion guide wire according to claim 6 wherein said flexible sheath is located within said third lumen.

9. An infusion guide wire according to claim 2 wherein said flexible sheath further comprises an imbedded metallic reinforcement.

10. An infusion guide wire according to claim 9 wherein said embedded metallic reinforcement further comprises a spring coil.

11. An infusion guide wire according to claim 9 wherein said embedded metallic reinforcement further comprises a braided structure.

12. An infusion guide wire according to claim 2 wherein said proximal end of the said flexible sheath is not coterminous with said proximal end of said outer coil.

13. An infusion guide wire according to claim 12 wherein said outer coil is space wound from said proximal end of said flexible sheath to said proximal end of said outer coil.

14. An infusion guide wire according to claim 6 wherein said inner coil is unifilar or multifilar, and wherein said inner coil is comprised of round, rectangular and/or triangular configured wire structure.

15. An infusion guide wire according to claim 9 wherein said inner coil in coterminous with said outer coil and is attached in junction with the outer coil at the said distal and proximal ends.

16. An infusion guide wire according to claim 6 wherein said inner coil is space wound at the said distal and proximal ends to allow for passage of fluid through interstices.

17. An infusion guide wire according to claim 1 wherein said distal tip marker is a coil and consists of a radiopaque material which is positioned over the distal end of said core wire and within said inner or outer coil lumens.

18. An infusion guide wire according to claim 17 wherein said radiopaque distal tip marker is positively attached at the distal end of said infusion guide wire concurrent with said core wire, inner coil, or outer coil.

* * * * *